(12) United States Patent
Nandi et al.

(10) Patent No.: US 8,168,228 B2
(45) Date of Patent: *May 1, 2012

(54) ANTIBIOTIC CLARITHROMYCIN MICROPELLET COMPOSITIONS

(75) Inventors: Indranil Nandi, Plainsboro, NJ (US); Mintong Guo, Plainsboro, NJ (US); Chad Michael Gassert, Hoboken, NJ (US); Franz Xaver Schwarz, Woergl (AT); Irina Kosilek, Kufstein (AT)

(73) Assignee: Sandoz AG, Basel (CH)

( * ) Notice: Subject to any disclaimer, the term of this patent is extended or adjusted under 35 U.S.C. 154(b) by 1639 days.

This patent is subject to a terminal disclaimer.

(21) Appl. No.: 10/768,562

(22) Filed: Jan. 30, 2004

(65) Prior Publication Data

US 2005/0084541 A1   Apr. 21, 2005

Related U.S. Application Data

(63) Continuation-in-part of application No. 10/688,551, filed on Oct. 17, 2003, now abandoned.

(51) Int. Cl.
*A61K 9/50* (2006.01)

(52) U.S. Cl. ...................................... 424/497

(58) Field of Classification Search ............... None
See application file for complete search history.

(56) References Cited

U.S. PATENT DOCUMENTS

| | | | |
|---|---|---|---|
| 4,842,866 A | 6/1989 | Horder et al. ................. | 424/468 |
| 5,633,006 A | 5/1997 | Catania et al. ................ | 424/441 |
| 5,788,987 A | 8/1998 | Busetti et al. ................. | 424/480 |
| 6,010,718 A | 1/2000 | Al-Razzak et al. ........... | 424/464 |
| 6,096,341 A | 8/2000 | Seth .............................. | 424/482 |
| 6,143,327 A | 11/2000 | Seth .............................. | 424/482 |
| 6,221,402 B1 * | 4/2001 | Itoh et al. ...................... | 424/494 |
| 6,331,316 B1 * | 12/2001 | Ullah et al. ................... | 424/482 |
| 6,451,345 B1 | 9/2002 | Percel et al. | |
| 6,565,877 B1 | 5/2003 | Mukherji et al. ............. | 424/441 |
| 6,642,276 B2 | 11/2003 | Wadhwa ....................... | 514/781 |
| 6,642,364 B2 | 11/2003 | Asensio Dominguez et al. ............................. | 536/7.2 |

FOREIGN PATENT DOCUMENTS

| | | |
|---|---|---|
| EP | 1213015 | 12/2002 |
| WO | WO 01/72284 | 10/2001 |
| WO | WO 02/17885 | 3/2002 |
| WO | WO 03/017981 | 3/2003 |
| WO | WO 03020242 | 3/2003 |
| WO | WO 03/082241 | 10/2003 |
| WO | WO 03/082248 | 10/2003 |

OTHER PUBLICATIONS

Friend D R: "Polyacrylate Resin Microcapsules for Taste Masking of Antibiotics" Journal of Microencapsulation, vol. 9, No. 4, Oct. 1, 1992, pp. 469-480.

* cited by examiner

*Primary Examiner* — Carlos Azpuru
(74) *Attorney, Agent, or Firm* — Luedeka Neely Group, P.C.

(57) ABSTRACT

An oral suspension comprising (a) an antibiotic composition which comprises coated micropellets and optionally one or more excipients, (b) additional excipients, and (c) a solvent, wherein said coated micropellets comprise (i) a core comprising at least one antibiotic; (ii) an inner coating comprising at least one cellulose polymer which is not an enteric coating polymer; and (iii) an outer coating comprising at least one enteric coating polymer, wherein said coated micropellets have a mean particle size of about 100 μm to about 650 μm. The oral suspension of the invention is characterized by a lack of bitter taste.

36 Claims, No Drawings

ANTIBIOTIC CLARITHROMYCIN MICROPELLET COMPOSITIONS

FIELD OF THE INVENTION

The present invention provides an antibiotic composition comprising coated micropellets.

BACKGROUND OF THE INVENTION

Antibiotics such as clarithromycin and erythromycin has been used in the treatment of common pediatric infections of the middle ear and upper respiratory tract, as well as certain forms of pneumonia that affects the elderly. However, such antibiotics are extremely bitter, and even when dissolved in trace quantities in a liquid dosage form are often perceived to be unpalatable. Administration of such antibiotics to children and the elderly poses a challenge as these patients experience difficulty in swallowing solid oral dosage forms. For these patients, antibiotics are typically provided in liquid forms, such as solutions, emulsions, and suspensions, which usually permit perceptible exposure of the antibiotic to the taste bud.

There is a need to mask the taste of such antibiotics in order to ensure patient compliance during therapy. Conventional taste masking techniques, such as the use of sweeteners, amino acids, and flavoring agents often are unsuccessful in masking the taste of highly bitter drugs and, consequently, other techniques need to be exploited for effectively masking the taste of these antibiotics.

One such technique involves the use of cation exchange resins, such as polysulfonic acid and polycarboxylic acid polymers, to adsorb amine drugs for taste masking and sustained release. However, this technique has limited applicability and is not capable of masking the taste of highly bitter drugs.

Coating of bitter drugs is another method which has been reported for taste masking. This technique alone may prove effective for moderately bitter drugs or in products where the coated particles are formulated as aqueous preparations before administration or are formulated in a non-aqueous medium. This technique has its limitations as coating of fine particles is usually technology intensive and coated granules are readily ruptured by chewing and compression.

Lipid-based microencapsulation is another technique used to taste mask the drugs. This technique requires highly sophisticated hot-melt granulation for producing fine particles, and may have adverse effects on heat sensitive molecules or restrict drug release adversely. U.S. Pat. No. 4,865,851 describes cefuroxime axetil in particulate form coated with an integral coating of lipid or a mixture of lipids.

U.S. Pat. No. 4,808,411 describes a taste-masked composition in the form of granules which contain clarithromycin and a carbomer acrylic acid polymer. The clarithromycin and carbomer are believed to be held together by both the ionic interactions between the amine group of clarithromycin and the carbonyl group of the carbomer and by the gel properties of the carbomer. This complex is further taste masked by coating.

U.S. Pat. No. 5,286,489 describes a porous drug-polymer matrix formed by admixing one or more bitter tasting active ingredient and a methyl methacrylic ester copolymer in at least a 1:1 by weight ratio of active ingredient to copolymer, effective to mask the taste of the drug. None of the examples described in U.S. Pat. No. 5,286,489 describe the effect of such polymers on the release of the drug from the matrix. While such a drug-polymer matrix may result in good taste-masking, the matrix may also retard the rate of drug release from the matrix to an extent which would be unacceptable for a conventional immediate-release formulation.

U.S. Pat. No. 5,633,006 describes a taste-masked composition containing a bitter pharmaceutical agent such as azithromycin, an alkaline earth oxide such as magnesium oxide, and a pharmaceutically acceptable carrier.

U.S. Pat. No. 6,565,877 describes a taste-masked composition containing a bitter tasting drug, such as clarithromycin, and a combination of two enteric polymers comprising a methacrylic acid copolymer and a phthalate polymer, wherein the ratio of methacrylic acid copolymer to phthalate polymer is between 1:9 or 9:1.

International Application WO 03/082248 describes a pharmaceutical composition containing erythromycin A or a derivative thereof, such as clarithromycin, and alginic agid.

International Application WO 03/082241 describes a pharmaceutical composition containing micronized clarithromycin. The clarithromycin has a particle size less than 35 microns.

SUMMARY OF THE INVENTION

The invention provides an antibiotic composition comprising coated micropellets and optionally one or more excipients, wherein said coated micropellets comprise (i) a core comprising at least one antibiotic; (ii) an inner coating comprising at least one cellulose polymer which is not an enteric coating polymer; and (iii) an outer coating comprising at least one enteric coating polymer, wherein said coated micropellets have a mean particle size of about 100 µm to about 650 µm.

According to another aspect, the invention provides an oral suspension comprising (a) an antibiotic composition which comprises coated micropellets and optionally one or more excipients, (b) additional excipients, and (c) a solvent, wherein said coated micropellets comprise (i) a core comprising at least one antibiotic; (ii) an inner coating comprising at least one cellulose polymer which is not an enteric coating polymer; and (iii) an outer coating comprising at least one enteric coating polymer, wherein said coated micropellets have a mean particle size of about 100 µm to about 650 µm.

According to another aspect, the invention provides a method for preparing an antibiotic composition comprising coated micropellets and optionally one or more excipients, said method comprising (A) mixing at least one antibiotic, and optionally one or more excipients, to form a premix; (B) adding a solvent, and optionally one or more excipients, to the premix formed in Step (A) and granulating in the presence of an impeller set at least at 50 rpm, to form a wet granulation; (C) drying the wet granulation, and optionally milling and screening the dried granules to form micropellets; and (D) coating the micropellets with an inner coating comprising at least one cellulose polymer which is not an enteric coating polymer; and (E) coating the micropellets from Step (D) with an outer coating comprising at least one enteric coating polymer to form coated micropellets, wherein said coated micropellets have a mean particle size of about 100 µm to about 650 µm.

The oral suspension of the invention is characterized by a lack of bitter taste.

DESCRIPTION OF THE INVENTION

The invention provides an antibiotic composition comprising coated micropellets and optionally one or more excipients, wherein said coated micropellets comprise (i) a core comprising at least one antibiotic; (ii) an inner coating comprising at least one cellulose polymer which is not an enteric coating polymer; and (iii) an outer coating comprising at least one enteric coating polymer, wherein said coated micropellets have a mean particle size of about 100 μm to about 650 μm. As used herein, "coated micropellets" refers to granules having a mean particle size of about 100 μm to about 650 μm, preferably 200 μm to about 500 μm. More preferably, at least about 90%, preferably 95%, of the coated micropellets have a particle size of about 100 μm to about 650 μm, most preferably, about 200 μm to about 500 μm.

Preferred antibiotics include the following: erythromycin; clarithromycin; fluoroquinolones, such as ciprofloxacin and norfloxacin; cephalosporins, such as cefuroxime and ceftriaxone; and tetracyclic antibiotics, for example, chloramphenicol, chlorpromazine, etc. A combination of antibiotics may also be used. Preferably, the antibiotic is clarithromycin. The antibiotic preferably has a particle size of about 0.1 μm to about 100 μm, more preferably 5 82 m to about 40 μm.

The antibiotic is present in an amount of from about 1 wt. % to about 80 wt. %, based on the total weight of the coated micropellet. Preferably, the antibiotic is present in an amount of from about 5 wt. % to about 50 wt. %, more preferably, about 20 wt. % to about 35 wt. %, based on the total weight of the coated micropellet.

Preferred cellulose polymers include the following: hydroxypropylmethyl cellulose, hydroxypropyl cellulose, methyl cellulose, ethyl cellulose, carboxymethylethyl cellulose, sodium carboxymethyl cellulose, and ethylcarboxyethyl cellulose. A combination of cellulose polymers may also be used. More preferably, the cellulose polymer is hydroxypropylmethyl cellulose or hydroxypropyl cellulose. Most preferably, the cellulose polymer is hydroxypropylmethyl cellulose.

Preferred enteric coating polymers include the following: cross-linked polyvinyl pyrrolidone; non-cross linked polyvinylpyrrolidone; hydroxypropylmethyl cellulose phthalate, hydroxypropylmethyl cellulose acetate succinate, cellulose acetate succinate; cellulose acetate phthalate, hydroxypropylmethyl cellulose acetate succinate, cellulose acetate trimellitate, hydroxypropyl methyl cellulose phthalate; hydroxypropyl methyl cellulose acetate succinate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester; ethyl cellulose succinate; carboxymethylamide; potassium methacrylatedivinylbenzene copolymer; polyvinylalcohols; polyoxyethyleneglycols; polyethylene glycol; sodium alginate; galactomannone; carboxypolymethylene; sodium carboxymethyl starch; copolymers of acrylic acid and/or methacrylic acid with a monomer selected from the following: methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate, or octadecyl acrylate, e.g. EUDRAGIT®-L and -S series, such as L100-55, L30D55, L100, S100, L12.5, and S12.5, available from Rohm; polyvinyl acetate; fats; oils; waxes; fatty alcohols; shellac; gluten; ethylacrylate-maleic acid anhydride copolymer; maleic acid anhydride-vinyl methyl ether copolymer; styrol-maleic acid copolymer; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; polyarginine; poly(ethylene); poly(propylene); poly (ethylene oxide); poly(ethylene terephthalate); poly(vinyl isobutyl ether); poly(vinyl chloride); and polyurethane. A combination of enteric coating polymers may also be used.

More preferably, the enteric coating polymer is selected from a copolymer of methacrylic acid and methyl methacrylate, and a copolymer of methacrylic acid and ethyl acrylate. Most preferably, the enteric coating polymer is poly(methacrylic acid, ethyl acrylate)1:1 (EUDRAGIT®-L30D 55 and EUDRAGIT®-L100-55).

It is within the scope of the invention for the antibiotic compositions to include one or more pharmaceutically acceptable excipients. Examples of such excipients are binders, diluents, plasticizers, anti-caking agents, fillers, solubilizing agents, disintegrants, lubricants, surfactants, flavorants, sweeteners, stabilizers, anti-oxidants, anti-adherents, preservatives, glidants, and pigments. A combination of excipients may also be used. Such excipients are known to those skilled in the art, and thus, only a limited number will be specifically referenced.

Preferred binders include, but are not limited to, starches, e.g., potato starch, wheat starch, corn starch; gums, such as gum tragacanth, acacia gum and gelatin; and polyvinyl pyrrolidone, e.g., Povidone. Polyvinyl pyrrolidone is a particularly preferred binder.

Preferred plasticizers include, but are not limited to, citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate. A combination of plasticizers may also be used. A preferred plasticizer for use with the cellulose polymer is polyethylene glycol, such as polyethylene glycol 600. A preferred plasticizer for use with the enteric coating polymer is a combination of triethyl citrate and glycerol monostearate.

Preferred fillers include, but are not limited to, microcrystalline cellulose, starch, pregelatinized starch, modified starch, dibasic calcium phosphate dihydrate, calcium sulfate trihydrate, calcium sulfate dihydrate, calcium carbonate, dextrose, sucrose, lactose, mannitol, and sorbitol. Lactose is a particularly preferred filler.

Examples of disintegrants include:
  (i) natural starches, such as maize starch, potato starch and the like, directly compressible starches, e.g., Sta-rx® 1500; modified starches, e.g., carboxymethyl starches and sodium starch glycolate, available as Primojel®, Explotab®, Explosol®; and starch derivatives, such as amylose;
  (ii) cross-linked polyvinylpyrrolidones, e.g., crospovidones, such as Polyplasdone® XL and Kollidon® CL;
  (iii) alginic acid and sodium alginate;
  (iv) methacrylic acid-divinylbenzene co-polymer salts, e.g., Amberlite® IRP-88; and
  (v) cross-linked sodium carboxymethylcellulose, available as, e.g., Ac-di-sol®, Primellose®, Pharmacel® XL, Explocel® and Nymcel® ZSX.

Additional disintegrants also include hydroxypropyl cellulose, hydroxypropylmethyl cellulose, croscarmellose sodium, sodium starch glycolate, polacrillin potassium, polyacrylates, such as Carbopol®, magnesium aluminium silicate and bentonite.

Examples of surfactants include:
1) reaction products of a natural or hydrogenated castor oil and ethylene oxide. The polyethyleneglycol-hydrogenated castor oils available under the trademark CREMOPHOR are especially suitable, such as CREMOPHOR RH 40 and CREMOPHOR RH 60. Also suitable are polyethyleneglycol castor oils such as that available under the trade name CREMOPHOR EL.
2) Polyoxyethylene-sorbitan-fatty acid esters, also called polysorbates, for example mono- and tri-lauryl, palmityl, stearyl and oleyl esters of the type known and commercially available under the trademark TWEEN.
   20 [polyoxyethylene(20)sorbitanmonolaurate],
   21 [polyoxyethylene(4)sorbitanmonolaurate],
   40 [polyoxyethylene(20)sorbitanmonopalmitate],
   60 [polyoxyethylene(20)sorbitanmonostearate],
   65 [polyoxyethylene(20)sorbitantristearate],
   80 [polyoxyethylene(20)sorbitanmonooleate],
   81 [polyoxyethylene(5)sorbitanmonooleate],
   85 [polyoxyethylene(20)sorbitantrioleate].
   A preferred product of this class is TWEEN 80.
   Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are most useful. Among the surfactants of Table 1, preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate.
3) Polyoxyethylene fatty acid esters, for example polyoxyethylene stearic acid esters of the type known and commercially available under the trademark MYRJ.
4) Polyoxyethylene-polyoxypropylene copolymers and block copolymers, for example of the type known and commercially available under the trademark PLURONIC, EMKALYX and POLOXAMER. Preferred products of this class are PLURONIC F68 and POLOXAMER 188.
5) Dioctylsulfosuccinate or di-[2-ethylhexyl]-succinate.
6) Phospholipids, in particular lecithins. Suitable lecithins include, in particular, soybean lecithins.
7) Propylene glycol mono- and di-fatty acid esters such as propylene glycol dicaprylate (also known and commercially available under the trademark MIGLYOL 840), propylene glycol dilaurate, propylene glycol hydroxystearate, propylene glycol isostearate, propylene glycol laurate, propylene glycol ricinoleate, and propylene glycol stearate.
8) Polyoxyethylene alkyl ethers such as those commercially available under the trademark BRIJ, e.g., Brij 92V and Brij 35.
9) Tocopherol esters, e.g., tocopheryl acetate and tocopheryl acid succinate.
10) Docusate salts, e.g., dioctylsulfosuccinate or related compounds, such as di-[2-ethylhexyl]-succinate.
A combination of surfactants may also be used.

Preferred sweeteners include, but are not limited to, artificial sweeteners such as aspartame, saccharin, and cyclamates; natural sweeteners such as sucrose, fructose, glucose, lactose, maltodextrin, and sodium glycolate; and mixtures of artificial and natural sweeteners, such as a mixture of aspartame and sucrose.

Preferred flavorants include, but are not limited to, cherry, strawberry, fruit punch, grape, cream, vanilla, chocolate, mocha, spearmint, cola, and the like.

Preferred pigments include, but are not limited to, titanium dioxide, iron oxide, and vegetable dyes.

Preferred diluents include, but are not limited to, dextrose, sorbitol, sucrose, lactose, mannitol, urea, potassium chloride, sodium chloride, gelatin, starch, methyl cellulose, ethyl cellulose, propyl cellulose, hydroxymethyl cellulose, hydroxyethyl cellulose, hydroxypropyl cellulose, hydroxypropyl methyl cellulose, silica, polyvinyl alcohol, polyvinylpyrrolidone, and magnesium stearate.

The antibiotic compositions of the invention are prepared by utilizing any one of a wide variety of different methods well known to one of ordinary skill in the art. The antibiotic compositions are preferably prepared by mixing at least one antibiotic, and optionally one or more excipients, in the presence or absence of a solvent, to form a premix. The premix is preferably in the form of a solid dispersion or a homogeneous suspension. The premix is preferably subject to high shear granulation, melt extrusion, wet granulation, or roller compaction, to form micropellets. The micropellets are preferably dried, or cooled in the case of melt extrusion, and optionally milled and/or screened. The micropellets are coated with an inner coating comprising at least one cellulose polymer which is not an enteric coating polymer; and an outer coating comprising at least one enteric coating polymer, to form coated micropellets.

In the case of high shear granulation, the high-shear granulation is preferably conducted in the presence of an impeller set at least at 50 rpm. More preferably, the impeller is set at about 300 rpm. Most preferably, the high-shear granulation is additionally conducted in the presence of a chopper which preferably is set at least at 1000 rpm, more preferably the chopper is set at about 2400 rpm.

In one embodiment of the invention, the antibiotic composition is prepared by a method comprising: (A) mixing at least one antibiotic, and optionally one or more excipients, to form a premix; (B) adding a solvent, and optionally one or more excipients, to the premix formed in Step (A) and granulating in the presence of an impeller set at least at 50 rpm, to form a wet granulation; (C) drying the wet granulation, and optionally milling and screening the dried granules to form micropellets; and (D) coating the micropellets with an inner coating comprising at least one cellulose polymer which is not an enteric coating polymer; and (E) coating the micropellets from Step (D) with an outer coating comprising at least one enteric coating polymer to form coated micropellets.

Drying techniques include spray-drying, fluid bed drying, flash drying, ring drying, micron drying, tray drying, vacuum drying, radio-frequency drying and microwave drying. A preferred drying technique is fluid bed.

Types of mills include fluid energy mill, ball mill or rod mill, hammer mill, cutting mill and oscillating granulator. More specifically, suitable mills include, Quadro, Fryma, Glatt Quick Sieve, Fluidaire, Fitzpatrick (Fitz mill), BTS mill and Tornado. A preferred mill is a Fitz mill.

The antibiotic compositions of the invention may be in the form of an oral suspension, capsule, caplet, powder, or tablet. In a preferred embodiment, the antibiotic compositions are in the form of an oral suspension. The oral suspension comprises (a) an antibiotic composition which comprises coated micropellets and optionally one or more excipients, (b) additional excipients, and (c) a solvent, wherein said coated micropellets comprise (i) a core comprising at least one antibiotic; (ii) an inner coating comprising at least one cellulose polymer which is not an enteric coating polymer; and (iii) an outer coating comprising at least one enteric coating polymer, wherein said coated micropellets have a mean particle size of about 100 μm to about 650 μm. The solvent for the oral suspension is preferably an aqueous solvent. The oral suspension is generally simply imbibed. Alternatively, the oral suspension may be mixed with foods or drinks.

Examples of additional excipients are binders, diluents, plasticizers, anti-caking agents, fillers, solubilizing agents, disintegrants, lubricants, surfactants, flavorants, sweeteners, stabilizers, anti-oxidants, anti-adherents, preservatives, glidants, and pigments. A combination of additional excipients may also be used. Preferred additional excipients include, sucrose, maltodextrin, potassium sorbate, silica, xanthan gum, titanium dioxide, and a flavorant.

The following non-limiting examples illustrate further aspects of the invention.

Example 1

Preparation of a Clarithromycin Composition

| Ingredient | Amount |
| --- | --- |
| Clarithromycin | 250.0 g |
| Lactose Monohydrate | 90.0 g |
| Starch 1500 | 95.0 g |
| Croscarmellose Na | 80.0 g |
| Polyvinylpyrrolidone K-90 | 6.0 g |
| Purified Water | q.s. |

The clarithromycin, lactose, starch and croscarmellose Na were mixed in a 2.5 L high-shear VG5 Glatt granulator for 5 minutes with an impeller set at 350 rpm and chopper set at 2000 rpm. Separately, the polyvinylpyrrolidone was mixed with water at room temperature until dissolved. The polyvinylpyrrolidone solution was added over a period of three minutes to the mixture containing clarithromycin and mixed in the granulator at 250 mL/min at the above settings. Mixing in the granulator was continued for an additional three minutes at the above settings to form wet granules. The wet granules were discharged and placed on a tray which was placed in an oven at 55° C. for 4 hours to form dried granules. The dried granules were screened through U.S. Standard Sieve No. 30, 40, 50, and 80 mesh screens. The granules collected on the 30 mesh screen were milled using a Quadro Co-mill equipped with a screen #62 to form micropellets. The micropellets were subjected to the screening procedure as described above and the particle size distribution was summarized in Table I. The yield of micropellets remaining on Sieves Nos. 40 to 80 was determined to be 83.5%, based on the total amount of ingredients.

TABLE I

| Sieve No. | Amount (g) |
| --- | --- |
| 30 | 18.6 |
| 40 | 207.1 |
| 50 | 136.7 |
| 80 | 49.7 |
| Pan | 59.2 |

Example 2

Preparation of Clarithromycin Composition

| Ingredient | Amount |
| --- | --- |
| Clarithromycin | 250.0 g |
| Lactose, regular | 90.0 g |
| Starch 1500 | 95.0 g |
| Ac-Di-Sol | 80.0 g |
| Polyvinylpyrrolidone K-90 | 6.0 g |
| Water | 415 mL |

The clarithromycin, lactose, starch and Ac-Di-Sol were mixed in a 2.5 L high-shear VG5 Glatt granulator for 5 minutes with a impeller set at 300 rpm and chopper set at 2400 rpm. Separately, the polyvinylpyrrolidone was mixed with water at room temperature until dissolved. The polyvinylpyrrolidone solution was added over a period of three minutes to the mixture containing clarithromycin and mixed in the granulator at 250 mL/min at the above settings. Mixing in the granulator was continued for an additional three minutes at the above settings to form wet granules. The wet granules were discharged and placed on a tray which was placed in an oven at 55° C. for 4 hours to form dried granules. The dried granules were screened using U.S. Standard Sieve No. 30, 40, 50, and 80 mesh screens. The granules collected on the 30 mesh screen were milled using a Fitzpatrick Mill equipped with a screen #65 to form micropellets. The micropellets were subjected to the screening procedure as described above and the particle size distribution was summarized in Table II. The yield of micropellets remaining on Sieves Nos. 40 to 80 was determined to be 81.15%, based on the total amount of ingredients.

TABLE II

| Sieve No. | Amount (g) |
| --- | --- |
| 20 | 4.0 |
| 30 | 57.1 |
| 40 | 120.7 |
| 50 | 179.8 |
| 60 | 29.2 |
| 80 | 36.0 |
| Pan | 45.8 |

Example 3

Preparation of Clarithromycin Composition

| Ingredient | Amount |
| --- | --- |
| Clarithromycin | 250.0 g |
| Lactose, regular | 75.0 g |
| Starch 1500 | 80.0 g |
| Ac-Di-Sol | 80.0 g |
| Polaxomer 188 | 34.0 g |
| Polyvinylpyrrolidone K-90 | 6.0 g |
| Water | 400 mL |

The clarithromycin, lactose, starch and Ac-Di-Sol were mixed in a 2.5 L high-shear VG5 Glatt granulator for 5 minutes with an impeller set at 400 rpm and no chopper blade.

Separately, the polyvinylpyrrolidone and Poloxamer 188 were mixed with water at room temperature until dissolved. The polyvinylpyrrolidone and polaxomer 188 solution was added over a period of fifteen minutes to the mixture containing clarithromycin and mixed in the granulator at 62 mL/min at the above settings. Mixing in the granulator was continued for an additional three minutes at the above settings to form wet granules. The wet granules were discharged and placed on a tray which was placed in an oven at 55° C. for 4 hours to from dried granules. The dried granules were screened through U.S. Standard Sieve No. 30, 40, 50, and 80 mesh screens. The granules collected on the 30 mesh screen were milled using a Fitzpatrick Mill equipped with a screen #65 to form micropellets. The micropellets were subjected to the screening procedure as described above and the particle size distribution was summarized in Table III. The yield of micropellets remaining on Sieves Nos. 40 to 80 was determined to be 58.0%, based on the total amount of ingredients.

TABLE III

| Sieve No. | Amount (g) |
| --- | --- |
| 20 | 36.0 |
| 30 | 82.5 |
| 40 | 100.7 |
| 50 | 130.6 |
| 60 | 29.2 |
| 80 | 40.0 |
| Pan | 57.4 |

Example 4

Preparation of Clarithromycin Composition

| Ingredient | Amount |
| --- | --- |
| Clarithromycin | 250.0 g |
| Polaxomer 188 | 75.0 g |

The clarithromycin and Poloxamer 188 were mixed in a container mixer with a rotation speed of 16 rpm, 5 minutes. The mixture was granulated, by using an extruder Theisson at a temperature of 70° C. The mass was collected, and cooled down to room temperature. The cooled granules were screened through a 0.5 mm sieve using an oscillating Frewitt. The granules were screened through a 200 μm sieve. The remaining granules were collected; the particle size distribution was summarized in Table III.
The fine particles <200 μm could be used for a repeated extrusion process.

Example 5

Preparation of Clarithromycin Composition

| Ingredient | Amount |
| --- | --- |
| Clarithromycin | 704.0 g |
| Polaxomer 188 | 176.0 g |
| Polyvinylpyrrolidone K-30 | 120.0 g |
| Water | 400.0 g |

The Poloxamer 188 and Polyvinylpyrrolidone K-30 were dissolved and mixed in a stainless steel container mixer with stirrer, the clarithromycin was suspended in this solution.

The solution was then spray-dried and agglomerated to pellets in a Glatt GPCG 30-WSA Modul as follows:

| | |
| --- | --- |
| Spray pressure of sprayguns | 2.5 bar |
| Nozzle size | 1.5 mm |
| Inlet air temperature | 110-130° C. |
| Outlet air temperature | 65-75° C. |

The dried pellets were sieved through a 500 μm sieve. The remaining pellets on the sieve could be re dissolved again.

Example 6

Preparation of Inner Coating (Cellulose Polymer)

| Ingredient | Amount |
| --- | --- |
| Hydroxypropylmethyl cellulose | 40 g |
| Water | 226 mL |
| Simethicone | 1 g |

Hydroxypropylmethyl cellulose, water and simethicone were mixed.

Example 7

Preparation of Outer Coating (Enteric Coating Polymer)

| Ingredient | Amount |
| --- | --- |
| Eugragit L30 D55 | 419.25 g |
| Polysorbate 80 | 1.50 g |
| Glyceryl Monostearate | 3.75 g |
| Triethyl Citrate | 18.75 g |
| Water | 306.38 mL |

Polysorbate 80, 1.5 g, was dissolved in 250 mL water with heating at 70° C. Glyceryl monostearate, 3.75 g, was added to the polysorbate solution at 70° C. and mixed. The mixture was allowed to cool with agitation. Eugragit L 30 D55, 419.25 g, which is in the form of a 30% aqueous dispersion was screened through a U.S. Sieve No. 40 mesh screen and the particles collected on the No. 40 mesh screen were collected. Triethyl Citrate, 18.75 g, was mixed with 56.38 mL of water to form a solution which was combined with the Eugragit dispersion, and added to the mixture containing polysorbate 80 and glyceryl monostearate, with agitation.

Example 8

Preparation of Coated Micropellets

The micropellets prepared in Example 1,2,3,4,5 were first coated with a cellulose polymer coating composition as prepared in Example 6 using a Wuster Column in a Glatt Fluid Bed Granulator. The coated micropellets were further coated with an enteric coating compositions as prepared in Example 7 using a Wuster Column in a Glatt Fluid Bed Granulator. The coated micropellets were subjected to the screening procedure as described above and the particle size distribution is summarized in Table IV.

TABLE IV

| Sieve No. | Amount (g) |
|---|---|
| 30 | 15.8 |
| 40 | 80.6 |
| 50 | 73.7 |
| 60 | 20.6 |
| 80 | 20.7 |
| Pan | 12.1 |

Example 9

Preparation of Clarithromycin Oral Suspension Products

| Clarithromycin Composition | Wt. % for 125 mg Clarithromycin | Wt. % for 250 mg Clarithromycin |
|---|---|---|
| Core | | |
| Clarithromycin | 3.845 | 7.690 |
| Copolymer of Ethylene Oxide and Propylene Oxide (Polaxomer 188 EP) | 1.003 | 2.003 |
| Polyvinylpyrrolidone (Povidone K-30) | 0.683 | 1.366 |
| Inner Coating | | |
| Hydroxypropylmethyl Cellulose (Pharmacoat 603) | 0.600 | 1.197 |
| Polyethylene Glycol 600 (Macrogel 6000) | 0.074 | 0.151 |
| Titanium Dioxide | 0.178 | 0.360 |
| Outer Coating | | |
| Poly(methacrylic acid, ethyl acrylate) Eudragit L30D55 | 2.197 | 4.391 |
| Triethyl Citrate | 0.329 | 0.658 |
| Glycerol Monostearate (Cutina GMS) | 0.065 | 0.132 |
| Polysorbate 80 (Tween 80) | 0.028 | 0.052 |
| Additional Excipients | | |
| Sucrose | 73.846 | 73.846 |
| Maltodextrin | 12.72 | 3.72 |
| Potassium Sorbate | 0.616 | 0.616 |
| Silicon Dioxide (Aerosil 200) | 0.153 | 0.153 |
| Citric Acid | 0.124 | 0.124 |
| Xanthan Gum | 0.153 | 0.153 |
| Titanium Dioxide | 1.076 | 2.308 |
| Fruit Punch Flavor | 2.308 | 1.076 |
| TOTAL | 100% | 100% |

The Poloxamer 188, Povidone K-30, and water were mixed in a stainless steel container mixer with stirrer, the clarithromycin was suspended in this mixture. The mixture was spray-dried and agglomerated to micropellets in a Glatt GPCG 30-WSA Modul. The dried micropellets were sieved through a 500 μm sieve.

Separately, Pharmacoat 603, Macrogel 6000, and titanium dioxide, were mixed to form an inner layer coating.

Separately, Tween 80 was dissolved in 250 mL water with heating at 70° C. Glyceryl monostearate was added to the Tween 80 solution at 70° C. and mixed. The mixture was allowed to cool with agitation. Eugragit L 30 D55, 419.25 g, which is in the form of a 30% aqueous dispersion was screened through a U.S. Sieve No. 40 mesh screen and the particles collected on the No. 40 mesh screen were collected. Triethyl Citrate was mixed with water to form a solution which was combined with the Eugragit dispersion, and added to the mixture containing Tween 80 and glyceryl monostearate, with agitation to form an enteric coating.

The micropellets prepared above were first coated with the inner coating using a Wuster Column in a Glatt Fluid Bed Granulator. The coated micropellets were further coated with the enteric coating using a Wuster Column in a Glatt Fluid Bed Granulator. The coated micropellets were mixed with the additional excipients using a V-Blender at 480 revolutions to form a clarithromycin powder composition. The clarithromycin powder composition was placed into a bottle. Water was added to the bottle and the bottle was shaken vigorously to form an oral suspension. The oral suspension is characterized by a lack of bitter taste.

While the invention has been described with particular reference to certain embodiments thereof, it will be understood that changes and modifications may be made by those of ordinary skill within the scope and spirit of the following claims:

What is claimed is:

1. An antibiotic composition comprising coated micropellets and optionally one or more excipients, wherein said coated micropellets comprise
   (i) a core comprising at least clarithromycin;
   (ii) an inner coating comprising at least one cellulose polymer which is not an enteric coating polymer; and
   (iii) an outer coating comprising at least one enteric coating polymer,
   wherein said coated micropellets have a mean particle size of about 100 μm to about 650 μm.

2. The composition according to claim 1, wherein the coated micropellets have a mean particle size of about 200 μm to about 500 μm.

3. The composition according to claim 1, wherein at least about 90% of the coated micropellets have a particle size of about 100 μm to about 650 μm.

4. The composition according to claim 3, wherein the coated micropellets have a particle size of about 200 μm to about 500 μm.

5. The composition according to claim 1, wherein the cellulose polymer is selected from the group consisting of hydroxypropylmethyl cellulose, hydroxypropyl cellulose, methyl cellulose, ethyl cellulose, carboxymethylethyl cellulose, sodium carboxymethyl cellulose, ethylcarboxyethyl cellulose, and combinations thereof.

6. The composition according to claim 5, wherein the cellulose polymer is selected from the group consisting of hydroxypropylmethyl cellulose and hydroxypropyl cellulose.

7. The composition according to claim 1, wherein the inner coating additionally comprises at least one plasticizer.

8. The composition according to claim 7, wherein the plasticizer is selected from the group consisting of acetyl-triethyl citrate, acetyl tributyl-, tributyl-, triethyl-citrate, glycerol diacetate, glycerol triacetate, acetylated monoglycerides, castor oil, dibutyl-phthalate, diamyl-phthalate, diethyl-phthalate, dimethyl-phthalate, dipropyl-phthalate, di-(2-methoxy- or 2-ethoxyethyl)-phthalate, ethylphthalyl glycolate, butylphthalylethyl glycolate, butylglycolate, propylene glycol, polyethylene glycol, diethyladipate, di-(2-methoxy- or 2-ethoxyethyl)-adipate, benzophenone, diethyl- and diburylsebacate, dibutylsuccinate, dibutyltartrate, diethylene glycol dipropionate, ethyleneglycol diacetate, ethyleneglycol dibutyrate, ethyleneglycol dipropionate, tributyl phosphate, tributyrin, polyethylene glycol sorbitan monooleate, sorbitan monooleate, and combinations thereof.

9. The composition according to claim 8, wherein the plasticizer is polyethylene glycol.

10. The composition according to claim 1, wherein the enteric coating polymer is selected from the group consisting of cross-linked polyvinyl pyrrolidone; non-cross linked polyvinylpyrrolidone; hydroxypropylmethyl cellulose phthalate, hydroxypropylmethyl cellulose acetate succinate, cellulose acetate succinate; cellulose acetate phthalate, hydroxypropylmethyl cellulose acetate succinate, cellulose acetate trimellitate, hydroxypropyl methyl cellulose phthalate; hydroxypropyl methyl cellulose acetate succinate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester; ethyl cellulose succinate; carboxymethylamide; potassium methacrylatedivinylbenzene copolymer; polyvinylalcohols; polyoxyethyleneglycols; polyethylene glycol; sodium alginate; galactomannone; carboxypolymethylene; sodium carboxymethyl starch; copolymers of acrylic acid and/or methacrylic acid with at least one monomer selected from the group consisting of methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate, and octadecyl acrylate; polyvinyl acetate; fats; oils; waxes; fatty alcohols; shellac; gluten; ethylacrylate-maleic acid anhydride copolymer; maleic acid anhydride-vinyl methyl ether copolymer; styrol-maleic acid copolymer; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; polyarginine; poly(ethylene); poly(propylene); poly(ethylene oxide); poly(ethylene terephthalate); poly(vinyl isobutyl ether); poly(vinyl chloride); polyurethane, and combinations thereof.

11. The composition according to claim 10, wherein the enteric coating polymer is selected from the group consisting of a copolymer of methacrylic acid and methyl methacrylate, and a copolymer of methacrylic acid and ethyl acrylate.

12. The composition according to claim 11, wherein the enteric coating polymer is a poly(methacrylic acid, ethyl acrylate).

13. The composition according to claim 1, wherein the outer coating additionally comprises at least one plasticizer.

14. The composition according to claim 13, wherein the plasticizer is triethyl citrate and glycerol monostearate.

15. The composition according to claim 1 in the form of a powder, an oral suspension, capsule, caplet, powder, or tablet.

16. A powder comprising the composition according to claim 1.

17. The composition according to claim 1, wherein the excipient is independently selected from the group consisting of a binder, diluent, plasticizer, anti-caking agent, filler, solubilizing agent, disintegrant, lubricant, surfactant, flavorant, sweetener, stabilizer, anti-oxidant, anti-adherent, preservative, glidant, pigment, and combinations thereof.

18. An oral suspension comprising (a) an antibiotic composition which comprises coated micropellets and optionally one or more excipients, (b) additional excipients, and (c) a solvent, wherein said coated micropellets comprise
(i) a core comprising at least clarithromycin;
(ii) an inner coating comprising at least one cellulose polymer which is not an enteric coating polymer; and
(iii) an outer coating comprising at least one enteric coating polymer,
wherein said coated micropellets have a mean particle size of about 100 μm to about 650 μm.

19. The oral suspension according to claim 18, wherein the excipient is independently selected from the group consisting of a binder, diluent, plasticizer, anti-caking agent, filler, solubilizing agent, disintegrant, lubricant, surfactant, flavorant, sweetener, stabilizer, anti-oxidant, anti-adherent, preservative, glidant, pigment, and combinations thereof.

20. The oral suspension according to claim 18, wherein the additional excipients are selected from the group consisting of a binder, diluent, plasticizer, anti-caking agent, filler, solubilizing agent, disintegrant, lubricant, surfactant, flavorant, sweetener, stabilizer, anti-oxidant, anti-adherent, preservative, glidant, pigment, and combinations thereof.

21. The oral suspension according to claim 18, wherein the inner coating additionally comprises a plasticizer.

22. The oral suspension according to claim 18, wherein the outer coating additionally comprises a plasticizer.

23. The oral suspension according to claim 18, wherein the solvent is an aqueous solvent.

24. An antibiotic composition comprising coated micropellets and optionally one or more excipients, wherein said coated micropellets comprise:
(i) a core comprising at least one antibiotic;
(ii) an inner coating comprising at least one cellulose polymer which is not an enteric coating polymer and at least one plasticizer selected from the group consisting of acetyl-triethyl citrate, acetyl tributyl-, tributyl-, triethylcitrate, glycerol diacetate, glycerol triacetate, acetylated monoglycerides, castor oil, dibutyl-phthalate, diamyl-phthalate, diethyl-phthalate, dimethyl-phthalate, dipropyl-phthalate, di-(2-methoxy- or 2-ethoxyethyl)-phthalate, ethylphthalyl glycolate, butylphthalylethyl glycolate, butylglycolate, propylene glycol, polyethylene glycol, diethyladipate, di-(2-methoxy- or 2-ethoxyethyl)-adipate, benzophenone, diethyl- and diburylsebacate, dibutylsuccinate, dibutyltartrate, diethylene glycol dipropionate, ethyleneglycol diacetate, ethyleneglycol dibutyrate, ethyleneglycol dipropionate, tributyl phosphate, tributyrin, polyethylene glycol sorbitan monooleate, sorbitan monooleate, and combinations thereof; and
(iii) an outer coating comprising at least one enteric coating polymer,
wherein said coated micropellets have a mean particle size of about 100 μm to about 650 μm.

25. The composition according to claim 24, wherein the coated micropellets have a mean particle size of about 200 μm to about 500 μm.

26. The composition according to claim 24, wherein at least about 90% of the coated micropellets have a particle size of about 100 μm to about 650 μm.

27. The composition according to claim 26, wherein the coated micropellets have a particle size of about 200 μm to about 500 μm.

28. The composition according to claim 24, wherein the cellulose polymer is selected from the group consisting of hydroxypropylmethyl cellulose, hydroxypropyl cellulose, methyl cellulose, ethyl cellulose, carboxymethylethyl cellulose, sodium carboxymethyl cellulose, ethylcarboxyethyl cellulose, and combinations thereof.

29. The composition according to claim 28, wherein the cellulose polymer is selected from the group consisting of hydroxypropylmethyl cellulose and hydroxypropyl cellulose.

30. The composition according to claim 24, wherein the plasticizer is polyethylene glycol.

31. The composition according to claim 24, wherein the enteric coating polymer is selected from the group consisting of cross-linked polyvinyl pyrrolidone; non-cross linked polyvinylpyrrolidone; hydroxypropylmethyl cellulose phthalate, hydroxypropylmethyl cellulose acetate succinate, cellulose acetate succinate; cellulose acetate phthalate, hydroxypropylmethyl cellulose acetate succinate, cellulose acetate trimellitate, hydroxypropyl methyl cellulose phthalate; hydroxypropyl methyl cellulose acetate succinate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester; ethyl cellulose succinate; carboxymethylamide; potassium methacrylatedivinylbenzene copolymer; polyvinylalcohols; polyoxyethyleneglycols; polyethylene glycol; sodium alginate; galactomannone; carboxypolymethylene; sodium carboxymethyl starch; copolymers of acrylic acid and/or methacrylic acid with at least one monomer selected from the group consisting of methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate, and octadecyl acrylate; polyvinyl acetate; fats; oils; waxes; fatty alcohols; shellac; gluten; ethylacrylate-maleic acid anhydride copolymer; maleic acid anhydride-vinyl methyl ether copolymer; styrol-maleic acid copolymer; 2-ethyl-hexyl-acrylate maleic acid anhydride; crotonic acid-vinyl acetate copolymer; glutaminic acid/ glutamic acid ester copolymer; carboxymethylethylcellulose glycerol monooctanoate; polyarginine; poly(ethylene); poly (propylene); poly(ethylene oxide); poly(ethylene terephthalate); poly(vinyl isobutyl ether); poly(vinyl chloride); polyurethane, and combinations thereof.

32. The composition according to claim 31, wherein the enteric coating polymer is selected from the group consisting of a copolymer of methacrylic acid and methyl methacrylate, and a copolymer of methacrylic acid and ethyl acrylate.

33. The composition according to claim 32, wherein the enteric coating polymer is a poly(methacrylic acid, ethyl acrylate).

34. The composition according to claim 24, wherein the outer coating additionally comprises at least one plasticizer.

35. The composition according to claim 34, wherein the plasticizer is triethyl citrate and glycerol monostearate.

36. The composition according to claim 24 in the form of a powder, an oral suspension, capsule, caplet, powder, or tablet.

* * * * *